United States Patent [19]

Schumann

[11] Patent Number: Plant 7,567

[45] Date of Patent: Jun. 25, 1991

[54] GERANIUM PLANT NAMED FISROM

[75] Inventor: Ingeborg Schumann, Hoehr-Grenzhausen, Fed. Rep. of Germany

[73] Assignee: Florfis AG, Binningen, Switzerland

[21] Appl. No.: 427,464

[22] Filed: Oct. 25, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner

[57] ABSTRACT

A new and distinct cultivar of Geranium plant named Fisrom, particularly characterized by the combined features of dark red flower color which does not fade, double flower type, good branching, dark green leaves, relatively short internodes, and red spider mite tolerance.

1 Drawing Sheet

The present invention comprises a new and distinct cultivar of Geranium, botanically known as *Pelargonium peltatum,* commonly known as Ivy Geranium and hereinafter referred to by the cultivar name Fisrom.

Fisrom is a product of a planned breeding program which had the objective of creating new Geranium cultivars with red flower color, double flower form, good branching, red spider mite resistance, fast rooting and good outside performance.

Fisrom was originated from a hybridization made by the inventor in a controlled breeding program in Galdar, Gran Canaria, Spain in 1983. The female parent was Yale, a cultivar having dark red flowers which later turn blue, slow rooting, and no resistance to red spider mite. The male parent of Fisrom was Tavira, a *Pelargonium peltatum* characterized by its light red flower color, vigorous growth habit, and long internodes.

Fisrom was discovered and selected as one flowering plant within the progeny of the stated cross by Ingeborg Schumann in May 1984 in a controlled environment in Hillscheid, Federal Republic of Germany.

The first act of asexual reproduction of Fisrom was accomplished when vegetative cuttings were taken from the initial selection in February 1985 in a controlled environment in Hillscheid, Federal Republic of Germany by, or under the supervision of, Ingeborg Schumann.

Horticultural examination of selected units initiated in February 1985 and continuing thereafter has demonstrated that the combination of characteristics as herein disclosed for Fisrom are firmly fixed and are retained through successive generations of asexual reproduction.

Fisrom has not been observed under all possible environmental conditions. The phenotype may vary significantly with variations in environment such as temperature, light intensity and daylength.

The following observations, measurements and comparisons describe plants grown in Hillscheid, Federal Republic of Germany, under greenhouse and outdoor conditions which approximate those generally used in commercial practice.

The following traits have been repeatedly observed and are determined to be basic characteristics, of Fisrom, which, in combination, distinguish this Geranium as a new and distinct cultivar:

1. Dark red flower color.
2. Medium green ivy shaped leaves.

3. Relatively short internodes.
4. Well branched habit.
5. Tolerance to red spider mite and diseases.
6. Fast rooting.

Of the many commercial cultivars known to the present inventor, the most similar in comparison to Fisrom is the maternal parent Yale. Reference is made to attached Chart A which compares certain characteristics of Fisrom to those same characteristics of Yale. In general comparison to Fisrom, the red flower color of Yale is not persistent, later turning to blue, and it has longer internodes, inferior rooting, and a much stronger susceptibility to red spider mite.

The accompanying photographic color photographic drawing shows typical flower and foliage characteristics of Fisrom, with the colors being as true as possible with illustrations of this type.

In the following description color references are made to The Royal Horticultural Society Colour Chart (R.H.S.). The color values were determined between 1:00 p.m. and 2:00 p.m. indoors on May 11, 1988 under 42,000 Lux light intensity at Hillscheid, Federal Republic of Germany.

Classification:

*Botanical.*—*Pelargonium peltatum* l'hert. cv Fisrom.

*Commercial.*—Ivy Geranium.

INFLORESCENCE

A. Umbel:

*Shape.*—Nearly semi-spherical, the pedicels forming an angle up to 180° C.

*Average diameter.*—Indoor, 8.5 cm; outdoor, 8.9 cm.

*Average depth.*—Indoor, 4.8 cm; outdoor, 4.9 cm.

*Peduncle length.*—Indoor, 18.0 cm; outdoor, 14.5 cm.

*Pedicel length.*—Indoor, 2.3 cm; outdoor, 1.9 cm.

*Number of flowers per umbel.*—8–14.

*Pedicel color.*—Green without anthocyanin, no "swellings".

*Peduncle color.*—Green, approximately 137D.

B. Corolla:

*Average diameter.*—Indoor, 5.3 cm; outdoor, 5.3 cm.

*Form.*—Double, 10–14 petals.

*Color (general tonality from a distance of three meters).*—Red, 46B.

*Color.*—Upper surface, in main body and at margin 46B with black stripes at the base of upper petals; lower surface carmine red, approximately 52A, with dark red veins.

C. Bud:

*Shape.*—Elongated.

*Color of sepals.*—Light green, approximately 141C.

*Color of petals.*—Carmine red, marbled.

D. Reproductive organs:

*Androecium.*—5–8 fertile anthers, with white filaments and black stamen, with plenty of orange-yellow pollen.

*Gynoecium.*—5–6 lobed stigma, white style and purple stigma, no seed set.

E. Spring flowering response period: In Hillscheid, Federal Republic of Germany in 1988, 25% of plants with at least 1 flower opened 10 weeks after planting of unrooted cuttings.

F. Outdoor flower production: The flower count in 1988 in Hillscheid, Federal Republic of Germany indicated between 45 and 50 flowers per plant for June through October observation period.

G. Durability: Good weather resistance.

PLANT

A. Foliage:

*Form.*—Ivy-shaped.

*Diameter of leaf.*—8–10 cm.

*Margin.*—Entire.

*Color (upper surface).*—Medium green about 137B–C.

*Color (zonation).*—Narrow ring-shaped brown zonation, about 166A; diameter of ring is about one third the diameter of the leaf; the conspicuousness of the zone varies from medium in spring and autumn to weak in summer.

*Tolerance to botrytis.*—Very good.

B. General appearance and form:

*Internode length.*—Medium, 4–5 cm.

*Branching pattern.*—5.5 branches per plant 13 weeks after planting of unrooted cuttings.

*Plant habit.*—Bushy, drooping, medium to vigorous growth.

*Length of branches.*—Up to 80 cm in August (32nd week).

CHART A

COMPARISON OF FISROM AND YALE

| | FISROM | YALE |
|---|---|---|
| Chlorophyll quality/leaf | medium to dark | medium |
| color | green 137B–C | green 137C |
| Markings on flower petals | weak (3) | medium (5) |
| conspicuousness ranging | | |
| from 1 (weak) to 9 (strong)-; | | |
| Pedicel swelling | absent | present |
| Low temperature tolerance | good | medium |
| Salt tolerance | good | bad |
| Branching habit | 5.5 | 4.0 |
| (number of branches) | | |
| Internode length | 4.5 cm | 5.3 cm |
| Resistance to pests | tolerant of red | no tolerance |
| Length of branches (in August) | spider mite | 105 cm |
| | 80 cm | |
| Flower color persistence | Excellent | Poor |

I claim:

1. A new and distinct cultivar of Geranium plant named Fisrom, as illustrated and described.

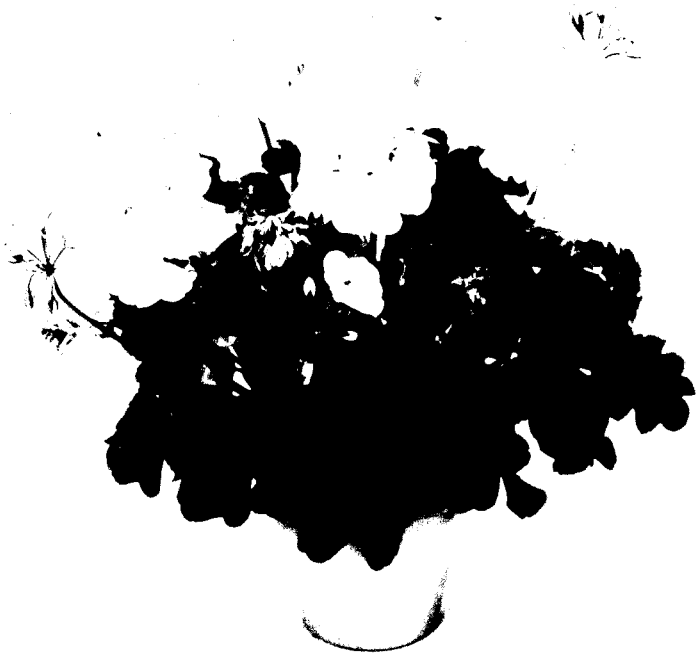

* * * * *